(12) United States Patent
Parthasaradhi Reddy et al.

(10) Patent No.: US 10,822,314 B2
(45) Date of Patent: Nov. 3, 2020

(54) PROCESS FOR THE PREPARATION OF A DUAL-ACTING ANGIOTENSIN RECEPTOR-NEPRILYSIN INHIBITOR COMPOUND

(71) Applicant: Hetero Labs Ltd., Hyderabad (IN)

(72) Inventors: Bandi Parthasaradhi Reddy, Hyderabad (IN); Kura Rathnakar Reddy, Hyderabad (IN); Adullla Venkat Narsimha Reddy, Hyderabad (IN); Bandi Vamsi Krishna, Hyderabad (IN)

(73) Assignee: Hetero Labs Ltd. (IN)

( * ) Notice: Subject to any disclaimer, the term of this patent is extended or adjusted under 35 U.S.C. 154(b) by 0 days.

(21) Appl. No.: 16/582,419

(22) Filed: Sep. 25, 2019

(65) Prior Publication Data

US 2020/0048210 A1 Feb. 13, 2020

Related U.S. Application Data

(62) Division of application No. 16/208,696, filed on Dec. 4, 2018, now Pat. No. 10,562,867, which is a division of application No. 15/752,943, filed as application No. PCT/IB2016/055097 on Aug. 26, 2016, now Pat. No. 10,214,497.

(30) Foreign Application Priority Data

Aug. 28, 2015 (IN) .......................... 4528/CHE/2015

(51) Int. Cl.
C07D 257/04 (2006.01)
A61K 31/41 (2006.01)

(52) U.S. Cl.
CPC ............ C07D 257/04 (2013.01); A61K 31/41 (2013.01)

(58) Field of Classification Search
CPC .............................. C07D 257/04; A61K 31/41
See application file for complete search history.

(56) References Cited

U.S. PATENT DOCUMENTS 10,214,497 B2 * 2/2019 Parthasaradhi Reddy ................. A61K 31/41
10,562,867 B2 * 2/2020 Parthasaradhi Reddy ................. C07D 257/04

FOREIGN PATENT DOCUMENTS

WO 2007/056546 A1 5/2007
WO 2016125123 A1 8/2016

OTHER PUBLICATIONS

International Search Report for PCT/IB2016/055097 dated Nov. 15, 2016.

* cited by examiner

Primary Examiner — Golam M Shameem
(74) Attorney, Agent, or Firm — Caesar Rivise, et al.

(57) ABSTRACT

The present invention relates to a process for preparing amorphous form of Sacubitril/Valsartan sodium salt of Formula-II and pharmaceutical composition comprising thereof.

2 Claims, 5 Drawing Sheets

Formula-II

PROCESS FOR THE PREPARATION OF A DUAL-ACTING ANGIOTENSIN RECEPTOR-NEPRILYSIN INHIBITOR COMPOUND

This application is a divisional application of U.S. application Ser. No. 16/208,696 filed Dec. 4, 2018, which is a divisional application of U.S. application Ser. No. 15/752,943 filed Feb. 15, 2018, which is a National Stage application of PCT/IB2016/055097 filed Aug. 26, 2016, which claims priority to IN 4528/CHE/2015 filed Aug. 28, 2015.

FIELD OF THE INVENTION

The present invention relates to a process for preparing amorphous form of LCZ696 and pharmaceutical composition comprising thereof.

BACKGROUND OF THE INVENTION

LCZ696 is known as Sacubitril/Valsartan trisodium hemipetahydrate and chemically known as 3-[N-[1(S)-(biphenyl-4-ylmethyl)-4-ethoxy-3(R)-methyl-4-oxobutyl]carbamoyl] propionic acid and N-pentanoyl-N-[2'-(1H-tetrazol-5-yl) biphenyl-4-ylmethyl]-L-valine trisodium hemipentahydrate and has the following structure, wherein designated as Formula-I.

Formula-I

Sacubitril is a neprilysin inhibitor pro-drug (AHU-377) and has now been tested in hypertension. LCZ696 has been approved in US under the trade name Entresto® as a tablet having dosage strengths 24MG, 26MG; 49MG, 51MG and 97MG, 103MG for treating chronic heart failure.

Pharmaceutical composition comprising Sacubitril or its pharmaceutically acceptable salt thereof and Valsartan or its pharmaceutically acceptable salt thereof is disclosed in U.S. Pat. No. 7,468,390 B2.

Figure 4:
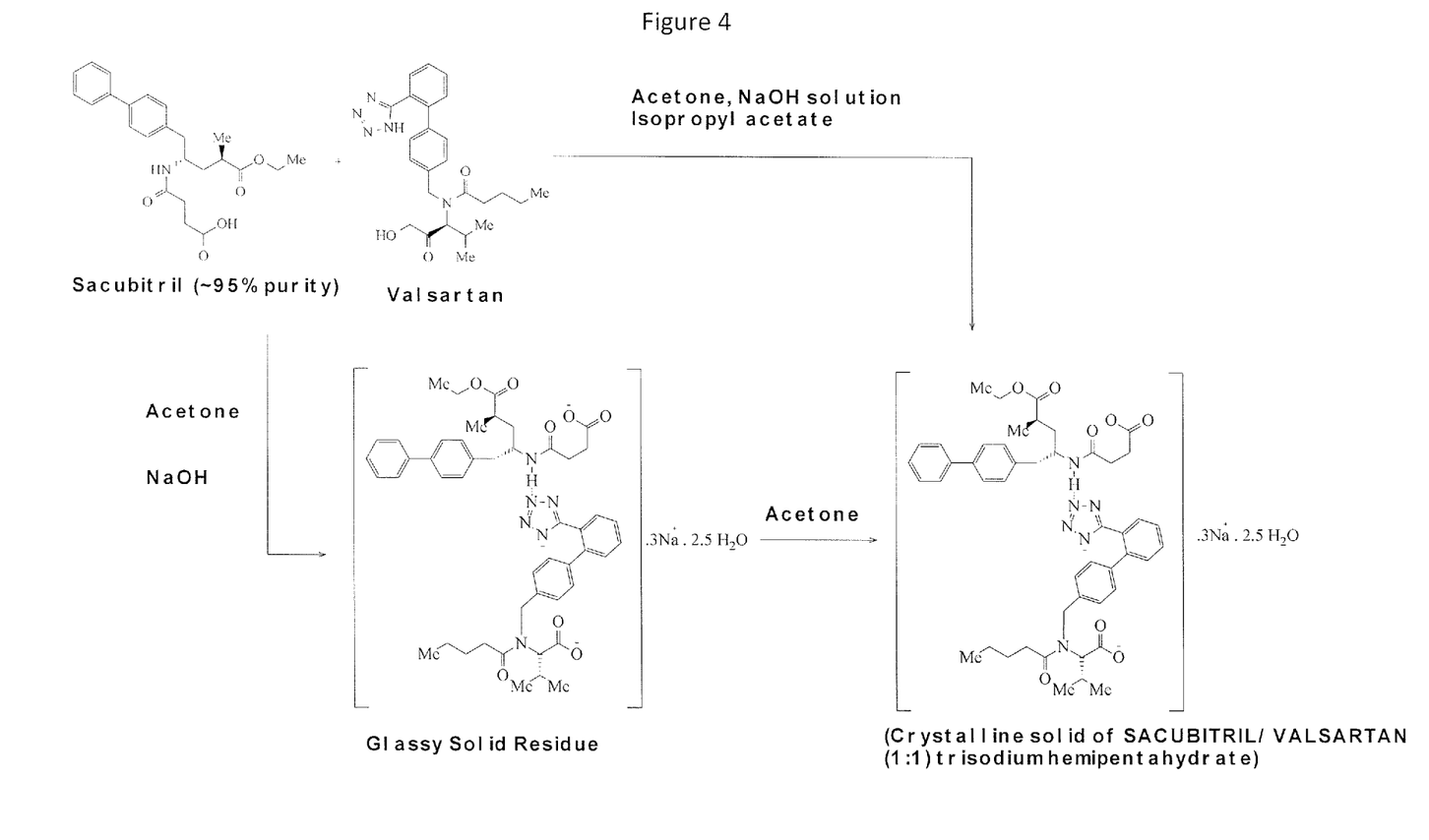
FIG. 4 shows the synthesis of Co-crystal of Sacubitril/Valsartan trisodium hemipentahydrate.

Mixed crystal/Co-crystal form of Sacubitril/Valsartan trisodium hemipentahydrate has been disclosed in U.S. Pat. No. 8,877,938 B2 of Novartis Pharmaceuticals. US'938 discloses the synthesis of Co-crystal of Sacubitril/Valsartan trisodium hemipentahydrate, which is as shown in FIG. 4.

Figure 5:
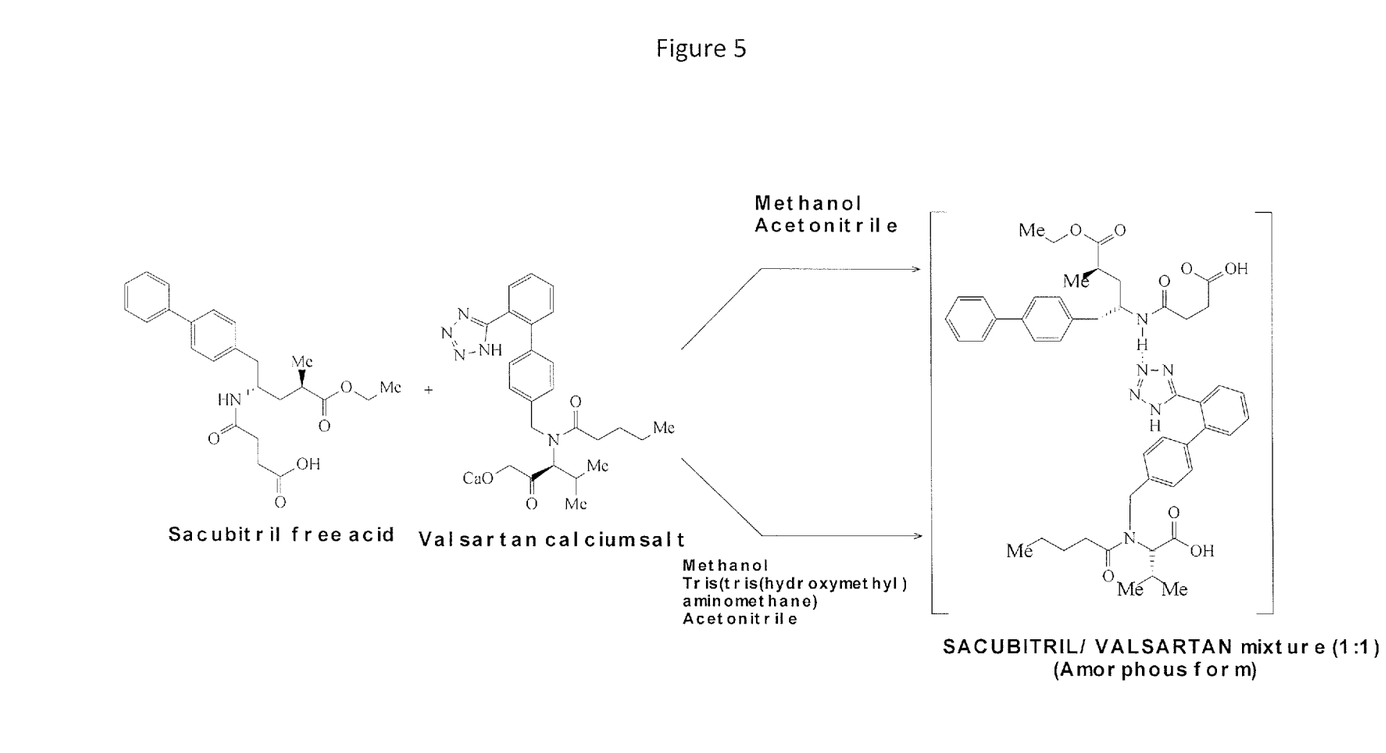
FIG. 5 shows the synthesis for the Linked pro-drug of amorphous form of Sacubitril/Valsartan.

US'938 also discloses the synthesis for Linked pro-drug of amorphous form of Sacubitril/Valsartan, which is as shown in FIG. 5.

CN 105693543 A discloses Sacubitril salts, wherein salt is selected from potassium salt, magnesium salt, t-butylamine salt, ethanolamine salt, piperazine salt, calcium, triethanolamine salt, trimethylamine salt.

CN 105461647 A discloses the Crystalline Form A of Sacubitril/Valsartan trisodium and Amorphous Forms α, β & γ of Sacubitril/Valsartan trisodium salt.

U.S. Pat. No. 7,468,390 B2 discloses the Triethanolamine and Tris(hydroxymethyl)aminomethane salts of Sacubitril.

The crystalline and amorphous form of Sacubitril/Valsartan sodium salt (LCZ696) were known, however still there is a need in prior-art to have a commercial, economical process to prepare stable amorphous form of the compound.

The present inventors have found a process for the preparation of amorphous form of Sacubitril/Valsartan sodium salt, wherein prepared. Amorphous form of Sacubitril/Valsartan sodium salt is stable, suitable for pharmaceutical formulation and is commercially, economically suitable for industrial scale.

Objectives

The objective of the present invention is to provide a process for the preparation of amorphous form of Sacubitril/Valsartan sodium salt, which is stable and has high yields and purity.

Another objective of the present invention is to provide a process for the preparation of amorphous form of Sacubitril/Valsartan sodium salt, which is commercially, economically suitable for industrial scale.

SUMMARY OF THE INVENTION

The present invention provides a process for the preparation of amorphous form of Sacubitril/Valsartan sodium salt of Formula-II:

Formula-II which comprises,
i) reacting sacubitril of Formula-III,

Formula-III with valsartan of Formula-IV

Formula-IV in a solvent,
ii) adding sodium source to the above solution;
iii) removing the solvent;
iv) adding an organic solvent, wherein organic solvent selected from group comprising of alcohol, ester and hydrocarbons;
v) removing the solvent;
vi) isolating the amorphous form of Sacubitril/Valsartan sodium salt of Formula-II, and
vii) optionally purifying the compound obtained in step (vi).

In another embodiment of the present invention provides a pharmaceutical formulation comprising a therapeutically effective amount of amorphous form of Sacubitril/Valsartan sodium salt of Formula-II and at least one pharmaceutically acceptable excipient.

DETAILED DESCRIPTION OF THE INVENTION

The present invention relates to a process for the preparation of amorphous form of Sacubitril/Valsartan sodium salt of Formula-II, which comprises reacting Sacubitril of Formula-III with Valsartan of Formula-IV in a solvent, wherein the solvent is selected from the group comprising of halogenated solvents, alcohols, ketonic solvents, ethers, esters hydrocarbons or mixture thereof, followed by adding a sodium source, wherein sodium source is selected from the group comprising of sodium hydroxide, sodium alkoxides, sodium 2-ethylhexanoate; thereafter removing the solvent.

In another embodiment of the present invention, after removing the solvent to the obtained reaction mass added organic solvent, selected from the group comprising of alcohol, ester and hydrocarbon or mixtures thereof and thereafter solvent is removed to isolate stable amorphous form of Sacubitril/Valsartan sodium salt of Formula-II.

In another embodiment of the present invention, the removal of the solvent is carried out by evaporation, fractional distillation, azeotropic distillation, rotavapour distillation, vacuum distillation and the like.

In another embodiment of the present invention, the amorphous form of Sacubitril/Valsartan sodium salt of Formula-II can be isolated, wherein isolation is carried out by known methods in the art, however by using filtration, centrifugation etc.

In another embodiment of the present invention, amorphous form of Sacubitril/Valsartan sodium salt of Formula-II can be optionally purified by conventional methods, dissolving the compound in a solvent and isolating the compound by cooling or by adding an anti-solvent.

In another embodiment of the present invention, the anti-solvent is the solvent wherein the compound is not dissolved.

In another embodiment throughout the invention, the halogenated solvents are selected from the group comprising of dichloromethane, ethylene dichloride, chloroform and the like; alcohols are selected from the group comprising of methanol, ethanol, isopropanol, butanol and the like; ketonic solvents are selected from the group comprising of acetone, methyl isobutyl ketone and the like; ethers are selected from the group comprising of tetrahydrofuran (THF), 2-methyl-tetrahydrofuran (MeTHF), diethyl ether, isopropyl ether, methyl isobutylether, dioxane and the like; esters are selected from the group comprising of ethyl acetate, isopropyl acetate and the like; hydrocarbons are selected from the group comprising of cyclohexane, hexane, heptane, n-hexane, n-heptane, toluene, xylene and the like; preferably ethanol, isopropanol, dichloromethane, isopropyl acetate, acetone, cyclohexane; more preferably dichloromethane, ethanol, cyclohexane, n-Hexane, acetone, isopropyl acetate.

In another embodiment throughout the invention, the mixture of solvents means two or more solvents.

In another embodiment throughout the invention, the sodium source is selected from the group comprising of Sodium hydroxide, Sodium alkoxides, Sodium 2-ethylhexanoate.

In another embodiment of the present invention, amorphous form of Sacubitril/Valsartan trisodium has water content (or) moisture content (MC) in the range of 2% to 7% w/w, preferably 2% to 6% w/w, more preferably 2.5% to 4% w/w; sodium content in the range of 6% to 9% w/w; the molar ratio of Sacubitril to Valsartan is about 1:1.

In another embodiment of the present invention, the amorphous form of Sacubitril/Valsartan trisodium obtained is highly hygroscopic in nature and becomes deliquescent at above 35% RH and hence must be handled at 30±5.0% RH. Further the analytical data such as Assay by HPLC and water content by KF needs to be performed simultaneously as it varies if performed differently.

In another embodiment of the present invention, the amorphous form of Sacubitril/Valsartan trisodium obtained is stable and data is as follows:

|  | Initial | 3 Months 5 ± 2° C. | 5 Months | Initial | 3 Months 25 ± 2° C. | 5 Months |
| --- | --- | --- | --- | --- | --- | --- |
| PXRD | Amorphous | Amorphous | Amorphous | Amorphous | Amorphous | Amorphous |
| Chromatographic purity by HPLC | 99.90% | 99.94% | 99.96% | 99.90% | 99.94% | 99.95% |
| Water content | 3.5% | 3.86% | 3.60% | 3.50% | 4.59% | 5.5% |

In another embodiment of the present invention provides a pharmaceutical formulation comprising a therapeutically effective amount of amorphous form of Sacubitril/Valsartan sodium salt of Formula-II and at least one pharmaceutically acceptable excipient. The Amorphous form of Sacubitril/Valsartan sodium may preferably be formulated into tablets, capsules, suspensions, dispersions, injectables or other pharmaceutical forms.

In another embodiment of the present invention, the pharmaceutically acceptable excipients selected from the group comprising of diluents such as calcium carbonate, calcium phosphate-dibasic, calcium phosphate-tribasic, calcium sulfate, microcrystalline cellulose, cellulose powdered, dextrates, dextrins, dextrose excipients, fructose, kaolin, lactitol, lactose, mannitol, sorbitol, starch, starch pregelatinized, sucrose, sugar compressible, sugar confectioners and the like or mixtures thereof; chelating agents such as ethylenetetraamineacetic acid, ethylenediaminetetraacetic acid (EDTA), and salts, derivatives and combinations thereof; disintegrants such as low-substituted hydroxypropylcellulose (L-HPC), sodium starch glycollate, carboxymethyl cellulose, calcium carboxymethyl cellulose, sodium carboxymethyl cellulose, croscarmellose sodium A-type (Ac-di-sol), starch, crystalline cellulose, hydroxypropyl starch, pregelatinized starch and the like and mixtures thereof; binders such as methyl cellulose, hydroxypropyl cellulose, hydroxypropyl methylcellulose, polyvinylpyrrolidone, gelatin, gum Arabic, ethyl cellulose, polyvinyl alcohol, pullulan, pregelatinized starch, agar, tragacanth, sodium alginate, propylene glycol, and the like; surfactants selected from the group comprising of both non-ionic and ionic (cationic, anionic and zwitterionic) surfactants suitable for use in pharmaceutical dosage forms. These include polyethoxylated fatty acids and its derivatives, for example, polyethylene glycol 400 distearate, polyethylene glycol-20 dioleate, polyethylene glycol 4-150 mono dilaurate, and polyethylene glycol-20 glyceryl stearate; alcohol-oil transesterification products, for example, polyethylene glycol-6 corn oil; polyglycerized fatty acids, for example, polyglyceryl-6 pentaoleate; propylene glycol fatty acid esters, for example, propylene glycol monocaprylate; mono and diglycerides, for example, glyceryl ricinoleate; sterol and sterol derivatives; sorbitan fatty acid esters and its derivatives, for example, polyethylene glycol-20 sorbitan monooleate and sorbitan monolaurate; polyethylene glycol alkyl ether or phenols, for example, polyethylene glycol-20 cetyl ether and polyethylene glycol-10-100 nonyl phenol; sugar esters, for example, sucrose monopalmitate; polyoxyethylene-polyoxypropylene block copolymers known as "poloxamer"; ionic surfactants, for example, sodium caproate, sodium glycocholate, soy lecithin, sodium stearyl fumarate, propylene glycol alginate, octyl sulfosuccinate disodium, and palmitoyl carnitine and the like or mixtures thereof; coloring agents, lubricants/glidants such as colloidal silicon dioxide, stearic acid, magnesium stearate, calcium stearate, talc, hydrogenated castor oil, sucrose esters of fatty acid, microcrystalline wax, yellow beeswax, white beeswax and the like or mixtures thereof.

In another embodiment of the present invention, Coloring agents include any FDA approved colors for oral use.

The invention of the present application will be explained in more detail with reference to the following examples, which should not be construed as limiting the scope of the invention in any manner.

EXAMPLES

Reference Example

Preparation of Sacubitril triethanolamine salt
(According to U.S. Pat. No. 7,468,390 B2)

Ethyl (2R,4S)-5-([1,1'-biphenyl]-4-yl)-4-amino-2-methylpetanoate hydrochloride (100 gm) was added to methylene chloride (1200 ml) and triethylamine (100 ml) at 25 to 30° C. The reaction mixture was cooled to 20 to 25° C. then succinic anhydride (40 gm) was added. The obtained clear solution was maintained for 2 hours at 25 to 30° C. and then cooled to 5 to 10° C. Hydrochloric acid (500 ml) was added then the temperature raised to room temperature and stirred for 10 minutes. To the reaction mixture was added diethyl ether (1800 ml) and stirred for 10 to 15 minutes.

Figure 3:
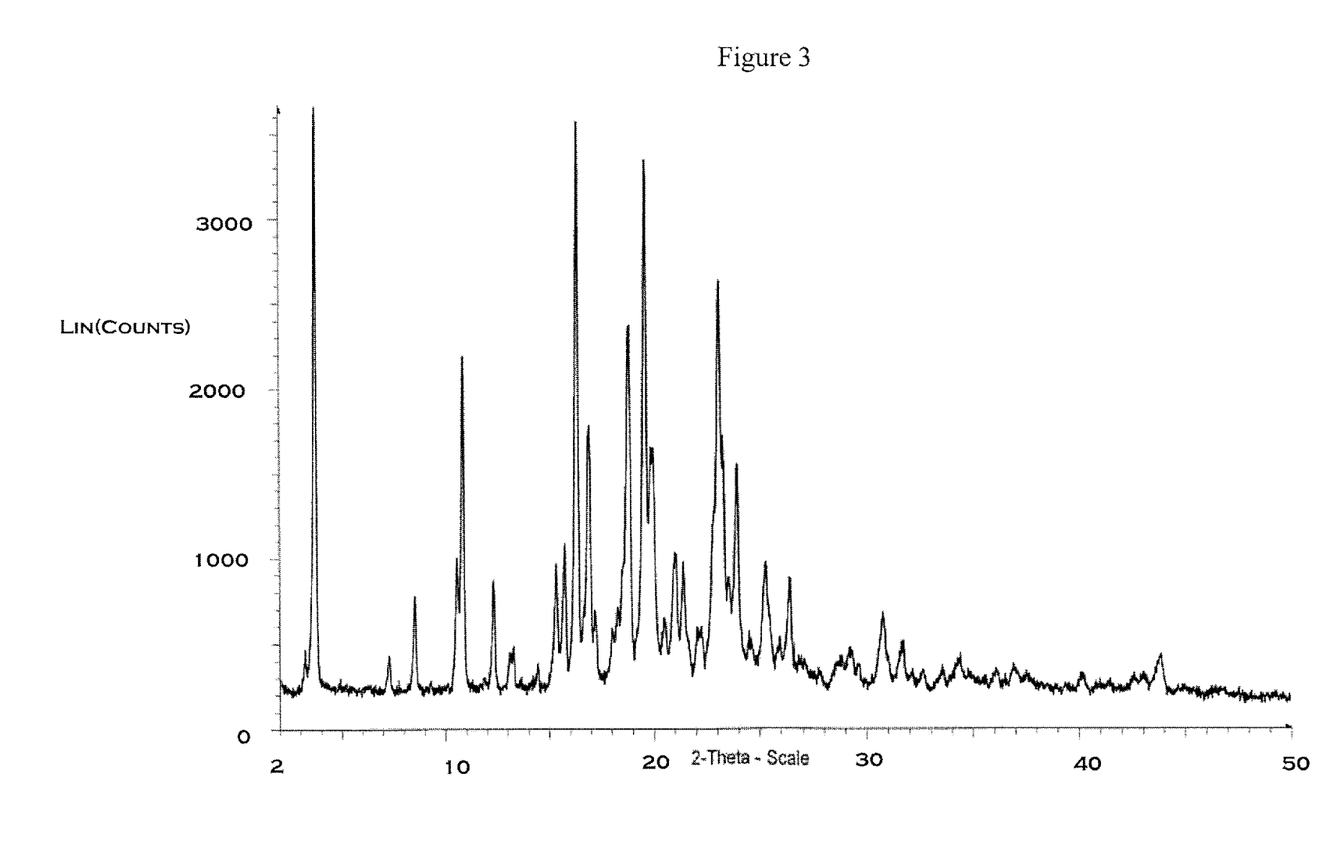
FIG. 3 is a powder X-ray diffractogram pattern of Crystalline Sacubitril triethanolamine salt.

To the obtained clear solution, triethanolamine (43 gm) solution in ethylacetate (360 ml) was added at 20 to 25° C. and stirred for 4 to 5 hours at room temperature. Filtered the obtained solid and washed with diethyl ether (200 ml). Dried the material at 40 to 45° C. for 8 to 10 hours to yield crystalline Sacubitril triethanolamine salt (138 gm). The PXRD depicts in FIG. 3.

Example 1

Preparation of Sacubitril triethanolamine salt

Ethyl (2R,4S)-5-([1,1'-biphenyl]-4-yl)-4-amino-2-methylpentanoate hydrochloride (100 gm) was added to methylene chloride (1200 ml) and triethylamine (100 ml) at 25 to 30° C. The reaction mixture was cooled to 20 to 25° C. then succinic anhydride (40 gm) was added. The obtained clear solution was maintained for 2 hours at 25 to 30° C. and then cooled to 5 to 10° C. Hydrochloric acid (500 ml) was added then the reaction mass temperature was raised to room temperature and stirred for 10 minutes. To the reaction mixture was added methyl tert-butyl ether (MTBE) (1800 ml) and stirred for 10 to 15 minutes.

Figure 1:
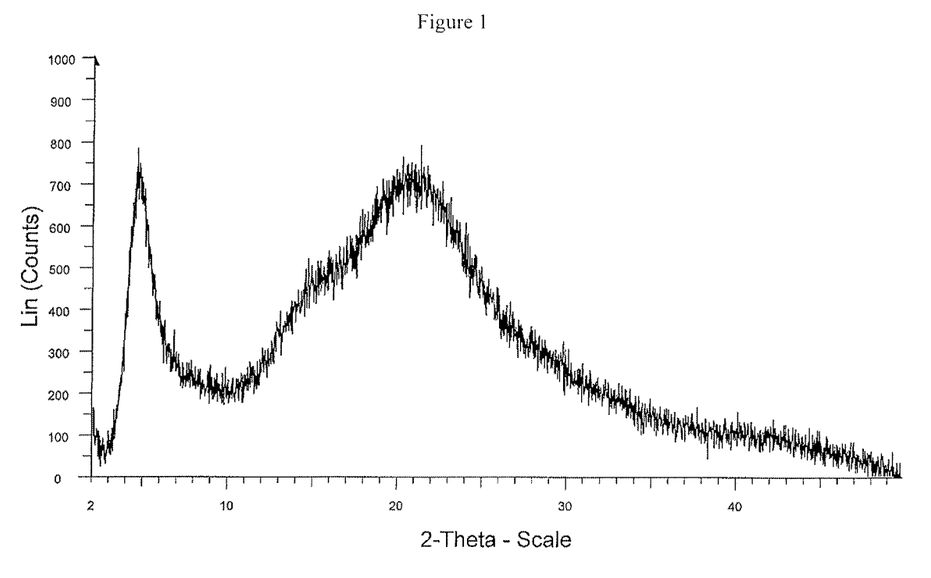
FIG. 1 is a powder X-ray diffractogram pattern of Amorphous form of Sacubitril/Valsartan trisodium.
Figure 2:
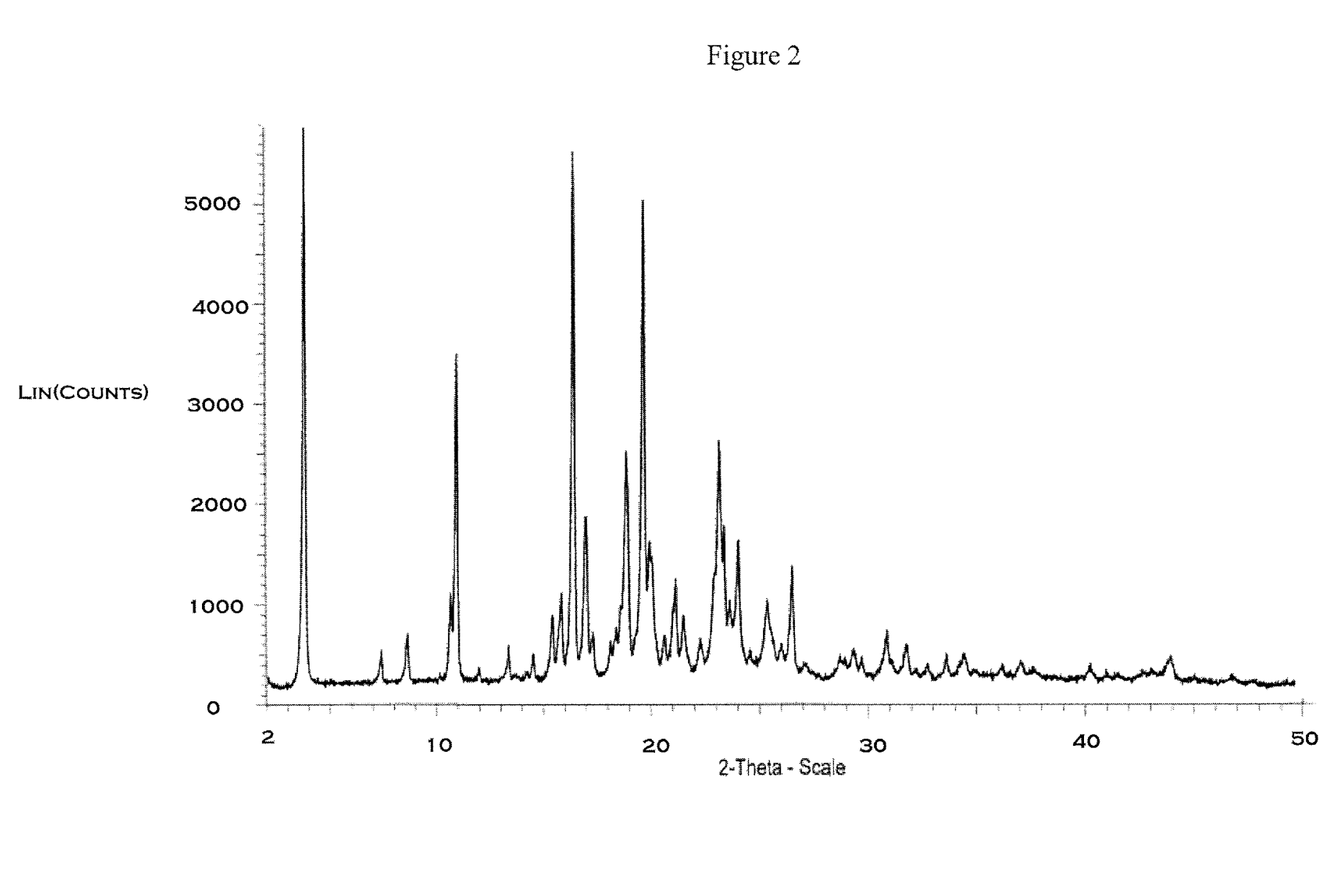
FIG. 2 is a powder X-ray diffractogram pattern of Crystalline Sacubitril triethanolamine salt.

To the obtained clear solution, triethanolamine (43 gm) solution in ethylacetate (360 ml) was added at 20 to 25° C. and stirred for 4 to 5 hours at room temperature. Filtered the obtained solid and washed with methyl tert-butyl ether (200 ml). Dried at 40 to 45° C. for 8 to 10 hours to yield crystalline Sacubitril triethanolamine salt (139 gm). The PXRD depicts in FIG. 2.
Chromatographic purity by HPLC: 99.74%
Content of triethanolamine: 27.93%.

Example 2: Preparation of Sacubitril

The Sacubitril triethanolamine salt (140 gm) was added to isopropyl acetate (1120 ml) at 25 to 30° C. The reaction mass was stirred for 10 minutes and cooled to 10° C. Hydrochloric acid (700 ml) was added and stirred for 10 to 15 minutes at room temperature and then layers were separated. Organic layer was washed with water and dried with $Na_2SO_4$ at 37 to 43° C. followed by distillation under vacuum and co-distilled with Acetone (280 ml) to yield Sacubitril.

Example 3: Preparation of Amorphous Form of Sacubitril/Valsartan Trisodium Salt

The obtained Sacubitril (in Example 2) and Valsartan (93.3 gm) were dissolved in Acetone (1764 ml) were added at room temperature and the obtained clear solution was cooled to 0 to 5° C. To the solution was added aq.sodium hydroxide solution (25 gm NaOH+79 ml of Water) by dropwise at 0 to 3° C. The reaction mixture was maintained for two hours at 0 to 3° C. Filtered the material on hyflo and washed with acetone (45 ml) and distilled off the solvent completely under vacuum pressure at below 45° C. To the obtained solid was added ethanol (300 ml), followed by distillation under vacuum to obtain amorphous form of Sacubitril/Valsartan trisodium salt.

n-Heptane (300 ml) was added to the above obtained solid at 25 to 30° C. and stirred for 40 to 50 minutes. Thereafter the reaction mass was concentrated and the obtained product was filtered and washed with n-heptane (180 ml) and dried at 45 to 50° C. to yield amorphous form of Sacubitril/Valsartan Trisodium Salt (190 gm).
Chromatographic purity by HPLC: 99.9%
M.C: 2.5% w/w
Content of Sodium: 6.8%

Example 4: Preparation of Amorphous Form of Sacubitril/Valsartan Trisodium Salt

The above obtained Sacubitril (in Example 2) was co-distilled with Acetone (280 ml) and Valsartan (93.3 gm) and Acetone (1764 ml) were added and the obtained clear solution was cooled to 0 to 5° C. To the solution was added aq.sodium hydroxide solution (25 gm of NaOH+79 ml of Water) by dropwise at 0 to 3° C. The reaction mixture was maintained for two hours at 0 to 3° C. Filtered the material on hyflo and washed with acetone (45 ml) and distilled off the solvent completely under vacuum pressure at below 45° C. The obtained solid was co-distilled with ethanol (300 ml), followed by co-distillation with cyclohexane (300 ml) at 45° C. To the obtained solid was added ethanol (300 ml), followed by distillation under vacuum to obtain amorphous form of Sacubitril/Valsartan trisodium salt.

Cyclohexane (300 ml) was added to the above obtained solid at 25 to 30° C. and stirred for 40 to 50 minutes. Thereafter the reaction mass was concentrated and the obtained product was filtered and washed with Cyclohexane (180 ml) and dried at 45 to 50° C. to yield amorphous form of Sacubitril/Valsartan trisodium salt (185 gm).
Chromatographic purity by HPLC: 99.91%
M.C: 2.5% w/w
Content of Sodium: 6.8%

Example 5: Preparation of Amorphous Form of Sacubitril/Valsartan Trisodium Salt

Ethyl (2R,4S)-5-([1,1'-biphenyl]-4-yl)-4-amino-2-methylpetanoate hydrochloride (100 gm) was added to methylene chloride (1200 ml) and triethylamine (100 ml) at 25 to 30° C. Succinic anhydride (40 gm) was added to the above reaction mixture and maintained for 2 hours at 25 to 30° C. and then cooled to 0 to 5° C. To the reaction mixture was added water (400 ml) and Hydrochloric acid (500 ml) and the temperature was raised to room temperature and stirred for 10 minutes. The layers were separated and washed with water (1600 ml) and 10% NaCl solution (800 ml), followed by drying with $Na_2SO_4$ to yield Sacubitril (118 gm).

Sacubitril (105 gm) and Valsartan (111 gm) were added to Acetone (2100 ml) at room temperature and stirred for 10 minutes. To the obtained clear solution was cooled to −2 to 5° C. To the above solution was added aq.sodium hydroxide solution by dropwise and maintained for two hours at −2 to 5° C. Filtered the obtained reaction mass and washed with acetone (210 ml) and the obtained filtrate was concentrated under vacuum at 35 to 45° C. The obtained solid was dried at 35 to 45° C. to yield amorphous solid. To the obtained solid was added cyclohexane (2 lts) and stirred for 2 hour. Filtered the solid and dried at 35 to 45° C. for 12 to 15 hours to yield Amorphous form of Sacubitril/Valsartan trisodium salt (220 gm).
Chromatographic purity by HPLC: 99.83%
M.C: 3.2% w/w
Content of Sodium: 6.9% w/w Example 6: Preparation of Amorphous Form of Sacubitril/Valsartan Trisodium Salt Sacubitril triethanolamine (50 gm), Isopropyl acetate (600 ml) and water (500 ml) were stirred for 10 minutes. To the obtained clear solution wad acidified with hydrochloric acid (250 ml) at 10 to 15° C. and washed with water (500 ml) and 10% NaCl solution (500 ml), followed by dried with $Na_2SO_4$ then filtered on hyflow bed. To the filtrate was added Valsartan (34.49 gm) at room temperature. NaOH solution (9.3 gm of NaOH+30 ml water) was added to the reaction mixture at 0-5° C. and maintained for 2 hours at room temperature. The reaction mass was concentrated under vacuum at 50° C. and co-distilled with isopropyl acetate (300 ml). To the obtained foamy solid was added isopropyl acetate (300 ml) and stirred for 10 minutes at room temperature. To the obtained clear solution was added n-Heptane (600 ml) and stirred for 1 hour, followed by filtration and dried at 45-50° C. to yield amorphous form of Sacubitril/Valsartan trisodium salt (65 gm).
Chromatographic purity by HPLC: 99.85%
M.C: 2.72% w/w
Content of Sodium: 6.71% w/w Example 7: Preparation of Amorphous Form of Sacubitril/Valsartan Trisodium Salt Sacubitril triethanolamine (140 gm), Isopropyl acetate (1680 ml) and water (700 ml) were stirred for 10 minutes at room temperature. The obtained solution was cooled to 10° C. acidified with hydrochloric acid (700 ml) at 10 to 15° C. and washed with water (1400 ml) and 10% NaCl solution (1400 ml), followed by dried with $Na_2SO_4$ and co-distilled with Acetone (280 ml) at 45° C. The reaction mass was cooled to room temperature and Valsartan (93 gm) and Acetone (1764 ml) were added. The reaction mixture was cooled to 0-5° C. and NaOH solution (25 gm of NaOH+79 ml of Water) was added and then stirred for 2 hours. Filtered on hyflow bed and washed with acetone (280 ml), followed by distilled the solvent completely under vacuum at 45° C. The obtained amorphous solid was co-distilled with ethanol (300 ml) at 45° C. and dried at 48-52° C. for 12 to 14 hours to yield amorphous form of Sacubitril/Valsartan trisodium salt (180 gm).
Chromatographic purity by HPLC: 99.83%
M.C: 3.32% w/w
Content of Sodium: 7.1% w/w Example 8: Preparation of Amorphous Form of Sacubitril/Valsartan Trisodium Salt Sacubitril (50 gm) and Valsartan (52.9 gm) were added to Isopropyl acetate (1000 ml) at room temperature and stirred for 10 minutes. To the obtained clear solution, Sodium 2-ethylhexanoate (68 gm) and isopropyl acetate (500 ml) solution was added and maintained for 16 to 18 hours. Water (250 ml) was added to the above reaction mass and stirred for 10 minutes. Aqueous layer was diluted with Ethanol (150 ml) followed by concentration to yield Amorphous solid. The obtained solid was dried at 50° C. to yield Amorphous Sacubitril/Valsartan trisodium salt (98 gm).
Chromatographic purity by HPLC: 99.89%
M.C: 3.68% w/w
Content of Sodium: 7.34% w/w

Example 9: Preparation of Amorphous Form of Sacubitril/Valsartan Trisodium Salt Sacubitril (50 gm) and Valsartan (52.9 gm) were added to Isopropyl acetate (1000 ml) at room temperature and stirred for 10 minutes. To the obtained clear solution, Sodium 2-ethylhexanoate (68 gm) and isopropyl acetate (500 ml) solution was added and maintained for 16 to 18 hours. Water (250 ml) was added to the above reaction mass and stirred for 10 minutes. Aqueous layer was diluted with Ethanol (150 ml) followed by concentration to yield Amorphous solid. The obtained solid was dried at 50° C. and was added cyclohexane (150 ml) then stirred for 2 hours. Filtered the solid and dried at 45 to 50° C. to yield Amorphous Sacubitril/Valsartan trisodium salt (95 gm).
Chromatographic purity by HPLC: 99.97%
M.C: 3.68% w/w
Content of Sodium: 7.34% w/w Example 10: Preparation of Amorphous Form of Sacubitril/Valsartan Trisodium Salt

Sacubitril (105 gm) and Valsartan (111 gm) were added to acetone (5250 ml) and stirred for 10 minutes. To the obtained clear solution was cooled to 0 to 2° C. To the solution was added aq.sodium hydroxide solution by dropwise at 0 to 2° C. The reaction mixture was maintained for two hours at 0° C. Heated to 20 to 30° C. and maintained for one hour at 20 to 30° C. Filtered the material and washed with acetone (210 ml) and then dried at 50° C. for 12 to 14 hours. To the obtained crystalline compound (179 gm) was added Ethanol (1800 ml) at 25-30° C. and stirred for 30 minutes. To the obtained clear solution was added charcoal (18 gm) and stirred for 10 minutes at 25-30° C. Filtered the material and washed with ethanol (180 ml). The reaction mass was concentrated at 45° C. and dried at 35-45° C. to yield Amorphous Sacubitril/Valsartan trisodium salt (170 gm).
Chromatographic purity by HPLC: 99.85%
M.C: 3.51% w/w
Content of Sodium: 7.66% w/w

What is claimed is:
1. A pharmaceutical formulation comprising a therapeutically effective amount of amorphous Sacubitril/Valsartan trisodium salt of Formula-II,

Formula-II

2. A process for preparing the pharmaceutical formulation comprising a therapeutically effective amount of Amorphous Sacubitril/Valsartan trisodium salt of Formula-II of claim 1 comprising the steps of:
    i) reacting sacubitril of Formula-III, Formula-III with valsartan of Formula-IV Formula-IV in a solvent, wherein solvent is selected from alcohol, ester, ketone and/or mixture thereof;

ii) adding sodium source to the above solution, wherein sodium source is selected from Sodium hydroxide, Sodium alkoxide and Sodium 2-ethylhexanoate;

iii) removing the solvent;

iv) adding an organic solvent, wherein organic solvent is selected from alcohol, ester, hydrocarbon solvent and/or mixture thereof;

v) removing the solvent;

vi) isolating the amorphous form of Sacubitril/Valsartan sodium salt of Formula-II, and vii) optionally purifying the compound obtained in step vi), and viii) preparing a pharmaceutical formulation comprising a therapeutically effective amount of the Amorphous Sacubitril/Valsartan trisodium salt of Formula-II and at least one pharmaceutically acceptable excipient.

* * * * *